(12) United States Patent
Weinberger et al.

(10) Patent No.: US 9,050,385 B2
(45) Date of Patent: Jun. 9, 2015

(54) METHODS OF DISINFECTION OR STERILIZATION

(71) Applicant: Saban Ventures Pty Limited, Alexandria (AU)

(72) Inventors: Ron Weinberger, Alexandria (AU); Michael Potas, Alexandria (AU)

(73) Assignee: Saban Ventures Pty Limited, Alexandria, New South Wales (AU)

( * ) Notice: Subject to any disclaimer, the term of this patent is extended or adjusted under 35 U.S.C. 154(b) by 0 days.

(21) Appl. No.: 13/752,854

(22) Filed: Jan. 29, 2013

(65) Prior Publication Data

US 2013/0202485 A1  Aug. 8, 2013

Related U.S. Application Data

(62) Division of application No. 12/525,658, filed as application No. PCT/AU2008/000108 on Jan. 31, 2008, now abandoned.

(30) Foreign Application Priority Data

Feb. 2, 2007  (AU) .............................. 2007900503

(51) Int. Cl.
*A61L 2/20*  (2006.01)
*A61L 2/28*  (2006.01)
(Continued)

(52) U.S. Cl.
CPC . *A61L 2/208* (2013.01); *A61L 2/20* (2013.01); *A61L 2/28* (2013.01); *A61L 2202/15* (2013.01); *A61L 2202/24* (2013.01); *B01D 61/362* (2013.01); *B01D 2311/13* (2013.01); *C01B 15/013* (2013.01); *B01D 61/36* (2013.01)

(58) Field of Classification Search
USPC .............................................. 422/124, 28, 33
See application file for complete search history.

(56) References Cited

U.S. PATENT DOCUMENTS 3,476,506 A  11/1969  Andersen et al.
3,481,689 A  12/1969  Rosdahl et al.
(Continued)

FOREIGN PATENT DOCUMENTS

EP  0679407  11/1995
GB  663720  12/1951
(Continued)

OTHER PUBLICATIONS

Content and Format of Premarket Notification [510(k)] Submissions for Liquid Chemical Sterilants/High Level Disinfectants, Jan. 3, 2000, Guidance for Industry and FDA Reviewers, CDRH, 59 pages.
(Continued)

*Primary Examiner* — Sean E Conley
(74) *Attorney, Agent, or Firm* — Senniger Powers LLP

(57) ABSTRACT

Methods for disinfecting or sterilizing an article are provided. One method includes vaporizing a solution comprising a biocide in a solvent having a first biocide:solvent ratio, directing a flow of the vapor to a first side of a membrane; directing an alternate flow of a gas to a second side of the membrane to increase the first biocide:solvent ratio on the first side to a second biocide:solvent ratio greater than the first biocide:solvent ratio thereby producing a concentrated vapor on the first side of the membrane, and contacting the article with the concentrated vapor for a time sufficient to disinfect or sterilize it.

19 Claims, 9 Drawing Sheets

(51) Int. Cl.
*B01D 61/36* (2006.01)
*C01B 15/013* (2006.01)

(56) References Cited

U.S. PATENT DOCUMENTS

| | | | |
|---|---|---|---|
| 3,950,247 | A | 4/1976 | Chiang et al. |
| 4,022,324 | A | 5/1977 | Schuster |
| 4,191,543 | A | 3/1980 | Peters |
| 4,296,068 | A | 10/1981 | Hoshino |
| 4,366,125 | A | 12/1982 | Kodera et al. |
| 4,680,163 | A | 7/1987 | Blidschun et al. |
| 4,718,985 | A | 1/1988 | Kjellander |
| 4,744,951 | A | 5/1988 | Cummings et al. |
| 4,958,529 | A | 9/1990 | Vestal |
| 4,978,430 | A | 12/1990 | Nakagawa et al. |
| 5,454,274 | A | 10/1995 | Zhu |
| 5,611,842 | A | 3/1997 | Friesen et al. |
| 5,681,433 | A | 10/1997 | Friesen et al. |
| 5,843,209 | A | 12/1998 | Ray et al. |
| 5,851,485 | A | 12/1998 | Lin et al. |
| 6,066,294 | A | 5/2000 | Lin et al. |
| 6,325,972 | B1 | 12/2001 | Jacobs et al. |
| 6,379,616 | B1 | 4/2002 | Sheiman |
| 6,500,465 | B1 | 12/2002 | Ronlan |
| 6,656,426 | B1 | 12/2003 | Wang et al. |
| 6,977,061 | B2 | 12/2005 | Lin et al. |
| 7,014,813 | B1 | 3/2006 | Watling et al. |
| 7,122,166 | B2 | 10/2006 | Parrish |
| 7,326,382 | B2 | 2/2008 | Adiga et al. |
| 2002/0119075 | A1 | 8/2002 | Jacobs et al. |
| 2003/0143110 | A1 | 7/2003 | Kritzler et al. |
| 2003/0183576 | A1 | 10/2003 | Ohara et al. |
| 2003/0192799 | A1 | 10/2003 | Addy et al. |
| 2004/0022673 | A1 | 2/2004 | Protic |
| 2004/0062692 | A1 | 4/2004 | Lin et al. |
| 2005/0252856 | A1 | 11/2005 | Parrish |

FOREIGN PATENT DOCUMENTS

| | | |
|---|---|---|
| GB | 2346095 | 8/2000 |
| JP | 55-137007 | 10/1980 |
| JP | 60-206408 | 10/1985 |
| JP | 60-220067 | 11/1985 |
| JP | 63-175602 | 7/1988 |
| JP | 02-273518 | 11/1990 |
| JP | 10-284458 | 10/1998 |
| JP | 2003-095617 | 4/2003 |
| JP | 2003-180802 | 7/2003 |
| JP | 2004-267755 | 9/2004 |
| WO | 9111374 | 8/1991 |
| WO | 9966961 | 12/1999 |
| WO | 02056988 | 7/2002 |
| WO | 2004037782 | 5/2004 |
| WO | 2004073827 | 9/2004 |
| WO | 2007014435 | 2/2007 |
| WO | 2007014436 | 2/2007 |
| WO | 2007014437 | 2/2007 |
| WO | 2007014438 | 2/2007 |

OTHER PUBLICATIONS

"Explanation of HMIS Ratings," obtained from http://www.paint.org/componentfdocman/cat_view/49-hmis.html on Feb. 10, 2012, 2 pages.

English translation of Office Action issued in Japanese Patent Application No. 2008-524316, mailed Nov. 29, 2011, provides brief description of JP 60-220067 for which no English translation is available. 5 pages.

International Search Report, PCT/AU2008/000108, dated Feb. 28, 2008, 5 pages.

Written Opinion, PCT/AU2008/000108, dated Feb. 28, 2008, 5 pages.

International Preliminary Report on Patentability, PCT/AU2008/000108, dated May 19, 2009, 9 pages.

Material Safety Data Sheet, Peracetic Acid, 35% MSDS, Sciencelab.com, created Oct. 10, 2005, Updated Nov. 1, 2010, 7 pages.

Material Safety Data Sheet, Ethanol Solution, Sigma-Aldrich Corporation, Version 3.1, Revised Jul. 12, 2011, Printed Feb. 10, 2012, 7 pages.

Material Safety Data Sheet, Hydrogen Peroxide Solutions Greater Than 60%, FMC MSDS Ref. No. 7722-84-1-5, Date Approved May 21, 2011, Revision No. 12, 11 pages.

McDonnell, G., et al., "Antiseptics and Disinfectants: Activity, Action, and Resistance," 1999, Clin Microbial Rev, 12/1:147-179.

English Translation of Office Action mailed Jun. 5, 2012 regarding related Japanese application Serial No. 2009-547491, 5 pgs.

Vapour Flow
Pathway

Counter Flow
Pathway

Diffusion Layer - Vapour and Counterflow Layers

Section AA

End Manifold Plates

Section BB

METHODS OF DISINFECTION OR STERILIZATION

REFERENCE TO CORRESPONDING APPLICATIONS

The present application is a divisional of U.S. application Ser. No. 12/525,658, which is a U.S. National Stage Application of International Application No. PCT PCT/AU2008/000108, filed Jan. 31, 2008, and is now abandoned, and claims priority to Australian Patent Application No. 2007900503, filed Feb. 2, 2007.

FIELD OF THE INVENTION

This invention relates to a method and apparatus for concentrating vapours, such as may be used for example in disinfecting or sterilizing a surface. The method and apparatus are particularly suited for disinfecting or sterilizing medical instruments but are not limited to that use.

BACKGROUND OF THE INVENTION

It is highly desirable to have sterilization processes and apparatus that avoid the need for temperatures above 60° C. while achieving the highest possible efficacy in pathogen destruction, especially when treating occluded, mated and lumen surfaces.

The use of high temperatures leads to complex and costly sterilization instruments, and more importantly, can damage many materials. This is a problem both in terms of patient safety and apparatus cost.

It is desirable that the disinfecting methods use hydrogen peroxide. Hydrogen peroxide at low concentrations is safe to transport, sell and handle and is extremely well known, with little or no regulatory barriers to its use. However, there are problems with those methods which require high concentration hydrogen peroxide as a starting material. For example, commercial vapour and plasma processes use as a starting material corrosive and irritating 60% peroxide solutions which requiring special packaging and handling precautions.

Any discussion of the prior art throughout the specification should in no way be considered as an admission that such prior art is widely known or forms part of common general knowledge in the field.

OBJECTS OF THE INVENTION

It is an object of the invention to provide improved methods and apparatus for disinfecting or sterilizing medical instruments which avoids or ameliorates at least some of the disadvantages of the prior art.

It is an object of preferred embodiments of the invention to provide improved methods an apparatus capable of concentrating and improving the properties of a vapour.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BRIEF STATEMENT OF INVENTION

According to a first aspect, the present invention provides apparatus for concentrating a first vapour in a mixture of a first vapour and at least a second vapour, the method comprising:

a vapour flow conduit;
a counter-flow conduit;
wherein at least a portion of said vapour flow conduit and said counter-flow conduit define respective opposed sides of a membrane; and wherein i) the membrane is selected to favour diffusion of the first vapour over at least the second vapour and/or ii) the operating conditions of the apparatus can be selected to favour diffusion of the first vapour over at least the second vapour.

The vapour flow and counter-flow may be in opposite directions, the same direction, or any other direction, eg perpendicular flows.

Preferably, the operating conditions which can be selected to favour diffusion of one vapour over one or more other vapours in the mixture of vapours include temperature or pressure control on either side of the membrane, or humidity or gas flow on an opposite side of the membrane to the mixture of vapours.

According to a second aspect, the present invention provides apparatus for concentrating a first vapour in a mixture of a first vapour and at least a second vapour, the method comprising:

a plurality of alternating vapour flow conduits and corresponding counter-flow conduits; and
wherein at least a portion of said each vapour flow conduit and an adjacent counter-flow conduit define respective opposed sides of a membrane; and wherein i) the membrane is selected to favour diffusion of the first vapour over at least the second vapour and/or ii) the operating conditions of the apparatus can be selected to favour diffusion of the first vapour over at least the second vapour.

The alternating vapour flow conduits and counter-flow conduits may be in a layered configuration. Alternatively, they maybe in a concentric, coaxial tubular arrangement.

Each vapour flow conduit comprises an inlet and an outlet. Each counter-flow conduit comprises an inlet and an outlet. Preferably, the vapour flow and counter-flow are in opposite directions. However, they may in the same direction, or any other direction, eg perpendicular flows.

Preferably the apparatus further comprises a vaporizer in communication with the vapour flow conduit.

Also preferably the apparatus further comprises a humidity control means for controlling the humidity of a counter-flow entering the counter-flow conduit According to a third aspect, the present invention provides apparatus for concentrating a first vapour in a mixture of a first vapour and at least a second vapour, the method comprising:

a vapour flow conduit;
at least two counter-flow conduits; and
wherein at least a portion of said vapour flow conduit and said counter-flow conduits define respective opposed sides of membranes; and wherein i) the membranes are selected to favour diffusion of the first vapour over at least the second vapour and/or ii) the operating conditions of the apparatus can be selected to favour diffusion of the first vapour over at least the second vapour.

According to a fourth aspect, the present invention provides apparatus for concentrating a first vapour in a mixture of a first vapour and at least a second vapour, the method comprising:

at least two vapour flow conduits;
a counter-flow conduit; and wherein at least a portion of said vapour flow conduit and said counter-flow conduits define respective opposed sides of membranes; and wherein i) the membranes are selected to favour diffusion of the first vapour over at least the second vapour and/or ii) the operating conditions of the apparatus can be selected to favour diffusion of the first vapour over at least the second vapour.

In one preferred embodiment, each vapour flow conduit comprises an inlet and an outlet, each counter-flow conduit comprises an inlet and an outlet, and the vapour flow and counter-flow are in the same or opposite directions.

In another preferred embodiment each vapour flow conduit comprises an inlet and an outlet, and the counter-flow conduit directs a counter flow in a direction at an angle to the vapour flow direction.

According to a fifth aspect the invention provides a method of producing a concentrated active from a solution comprising an active in a solvent and having a first active:solvent ratio, said method comprising the steps of:

(1) vaporizing the solution to form a vapour wherein the concentration of active is at about said first ratio, (2) providing a flow of the vapour to a first side of a membrane; and (3) providing an alternate flow of a gas to a second side of the membrane whereby to increase said first active:solvent ratio on the first side to a second active:solvent ratio greater than the first active:solvent ratio.

According to a sixth aspect the present invention provides a method for concentrating a vapour comprising the steps of (1) providing a flow of a vapour of an active in a solvent and having a first active:solvent ratio to a first side of a membrane; and (2) providing an alternate flow of a gas to a second side of the membrane whereby to increase said first active:solvent ratio on the first side to a second active:solvent ratio greater than the first active:solvent ratio.

The concentrated vapour is preferably used to disinfect and/or sterilize an article.

The vapour is preferably a vapour of water and a biocide, ie the solvent is preferably water. Most preferably, the biocide or active is a peroxy compound, most preferably hydrogen peroxide. The present invention encompasses any situation where the active:solvent ratio is increased. The active may be present in very small quantities, such as 0.1% (or less) of the total active plus solvent and concentrated up to the point where all or substantially all of the solvent is removed, ie 100% active.

Hydrogen peroxide is typically sold as a 30-35 wt % solution in water, so in one embodiment the first active to solvent ratio is preferably below 35 wt %, and more preferably about 30 wt %.

The second active:solvent ratio may be any level up to and including 100%. In some cases, it is preferably above 60 wt %, and more preferably about 70 wt %, and in some preferred embodiments, even above 80% or 90%. The counter-flow of gas is preferably provided at a rate and for a time such that the second ratio is not capable of further increase.

For preference the gas is air, more preferably humidity conditioned air.

The semi-permeable fabric or membrane may be a woven, or non-woven fabric, or it may be a sheet or film or a combination thereof and may be of a single layer or multilayer construction.

The term "membrane" is used herein where the context permits to include all such fabrics and membranes having the selected properties. The membrane may be hydrophobic or hydrophilic in nature.

In this specification where the context permits references to a fabric or membrane include fabrics or membranes suitable for pervaporation as well those only suitable for simple permeation, and references to permeation include references to pervaporation. Other membranes than those described and membranes may be used and may include membranes suitable for pervaporation, or other permeable or semi-permeable membranes. A highly preferred membrane is Kimguard™

In a highly preferred embodiment a peroxide solution having an initial concentration of at least 3-6%, preferably 20%-35%, and more preferably 30%-35%, is vapourized.

Water vapour permeates through the membrane, leaving peroxide vapour behind. The peroxide in the vapour becomes more concentrated.

The more concentrated peroxide vapour is significantly more effective as a sterilant than prior art hydrogen peroxide vapour possibly because a much higher concentration of sterilant is obtainable per unit volume.

Air permeating into the vapour flow conduit is sterile by virtue that the membrane is not penetrable by micro-organisms.

According to a seventh aspect the invention provides a process according to any one of the preceding aspects wherein the membrane is selected to remove one or more vapours by a process of pervaporation.

Although the invention is herein described with reference to hydrogen peroxide as the biocide, the invention is equally applicable when the biocide was another peroxide or peroxy compound, or could be used with other known vaporizable biocides or biocides when dissolved in suitable solvents (which need not be aqueous). Preferably the vapour is subsequently removed by an exterior current of air (or other fluid) adjacent the membrane exterior.

According to an eighth aspect the invention provides a method for disinfecting or sterilizing an article comprising the steps of:

(1) vaporizing a solution consisting of an active in a solvent and having a first active:solvent ratio, (2) providing a flow of the vapour to a first side of a membrane; and (3) providing an alternate flow of a gas to a second side of the membrane whereby to increase said first active:solvent ratio on the first side to a second active:solvent ratio greater than the first active:solvent ratio, and (4) contacting the vapour from step 2 with the article for a time sufficient to disinfect or sterilize it.

In one preferred embodiment the method is conducted at atmospheric pressure or above.

In another preferred embodiment the method is conducted at below atmospheric pressure.

Preferably the counter-flow of gas is provided at a rate and for a time such that the second ratio reaches an equilibrium ratio beyond which it will not increase.

According to a ninth aspect the invention provides a method for disinfecting or sterilizing an article comprising the steps of (1) enclosing the article inside a container having a wall of which at least a part is a membrane;

(2) providing a vapour of an active in a solvent and having a first active:solvent ratio, (3) providing an alternate flow of a gas to a side of the membrane external to the container whereby to increase the first active:solvent ratio to a second active:solvent ratio greater than the first active:solvent ratio, and produce a concentrated vapour; and (4) allowing the article to remain in contact with the concentrated vapour for a time sufficient to permit sterilization.

Preferably the membrane is impenetrable by microorganisms and the article is sterilized and stored sterile in the container.

In preferred embodiments a hydrogen peroxide solution in water of for example 35% concentration is firstly vapourised and then the vapour is concentrated in one chamber by removal of water through a membrane. The concentrated vapour is then admitted to another chamber which is desirably a bag or other container having a membrane as defined as a wall or part thereof which is then sealed. This allows the article to be sterilized and stored sterile in the second container and permits removal of residual hydrogen peroxide and water. Preferably the invention provides in particular, a vapour having a peroxide concentration of >70 wt % and a water concentration of less than 30 wt %.

DESCRIPTION OF PREFERRED EMBODIMENTS

The invention will now be described in the context of sterilization and disinfection, but it will be appreciated that the pre-concentrators and pre-concentration methods of the present invention can be used in a variety of fields where concentrated vapours are desired, eg drug delivery, painting/printing, food preparation, materials fabrication and the like. For example, a number of such processes have been described (U.S. Pat. No. 6,451,254, U.S. Pat. No. 6,673,313 and U.S. Pat. No. 6,656,426) all of which require involve concentrating a hydrogen peroxide solution by lowering the pressure to preferentially evaporate water and removing the water through a vacuum pump prior to vaporizing the solution.

Figure 3:
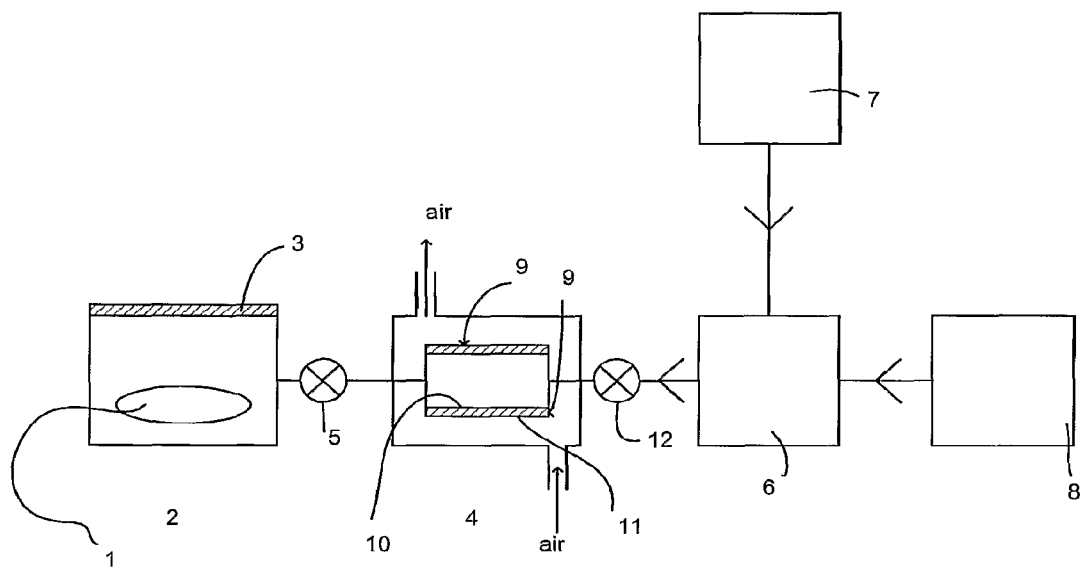
FIG. 3 is a diagram of a sterilizing apparatus showing the pre-concentrator of the present invention

The general pre-concentration process of the present invention takes place in the context of the following, and can be seen with reference to FIG. 3. An article to be sterilized 1 is placed into a sterilization chamber 2. The sterilization chamber 2 may be any suitable container, but advantageously is a bag made from a membrane, or a sealed container having a window of a membrane 3.

A pre-concentrator chamber of the present invention 4 is connected upstream of the sterilization chamber 2. The sterilization chamber 2 and pre concentrator 4 are connected such that flow between the pre-concentrator and sterilizing chamber can be opened or closed by way of a valve 5.

An vaporizer 6 is connected upstream of the pre-concentrator chamber. A hydrogen peroxide solution having a starting concentration preferably of around 30-35% is vapourized.

In the vaporizer, the aqueous hydrogen peroxide is heated, for example, by way of an electrically heated surface, such as a hot plate, and is then moved away from the vaporization area, for example, by an impeller, blower or the like. Alternatively, if the aqueous hydrogen peroxide is applied by a jet directed onto the hot plate, the jet may move the vapour. Alternatively, the vapour may be drawn from the vaporizer by a vacuum.

The vaporizer 6 may be fed with sterilant solution on a continuous or intermittent basis from a bulk supply 7, or may be provided with a single shot dosing system for example a cartridge providing sufficient solution for one or a plurality of sterilization cycles. Alternatively, a sterilant solution may be provided pre-packed in a capsule which may be placed in an adapted vaporizer so that the capsule is in contact with the heating element of the vaporizer. In this case means are provided for piercing the capsule so that it is able to release the solution as a vapour.

The unconcentrated hydrogen peroxide vapour is then propelled into the pre-concentrator 4 by means of a fan 8 upstream of the vaporizer 6. The vapour formed by the vaporizer 6 is entrained in a gas stream which in the preferred embodiment is air. It is a significant advantage of preferred embodiments of the invention over prior art that they do not require a source of filtered sterile air. Instead the invention is able to draw non-sterile air from the sterilization chamber, and sterilize it while recirculating it in use. However, if preferred, aseptic filtered air could be employed. The gas stream is not necessarily air, and could for example be an inert gas such as nitrogen, or argon; or could be oxygen or ozone.

In general terms, the pre-concentrator 4 works by exposing the vapour to one face 10 of a membrane 9 while an air current moves across the other face 11 of this membrane. This leads to preferential evaporation of the water from the vapour, causing it to become more concentrated with respect to hydrogen peroxide. As a result of the preferential evaporation of water, the vapour inside the pre concentrator 4 become more concentrated with respect to hydrogen peroxide with the concentrations approaching 60% or upwards.

Once formed, the highly concentrated vapour then makes contact with the article to be sterilised.

There are two possible preferred modes of operation of the pre-concentrator:

In the first operating mode, which is a batch-wise concentration process, the pathway between the concentrator 4 and sterilizing chamber 2 is shut and a vapour of 35% hydrogen peroxide in water is driven into the pre-concentrator chamber 4. The pre-concentrator chamber is then isolated (by shutting both valves 5 and 12) and the vapour in the pre-concentrator 4 is then concentrated. Concentration in the pre-concentrator takes place until the maximum concentration of peroxide is achieved. Once this maximum concentration is achieved, the pathway between the pre-concentrator and sterilizing chamber is opened by opening valve 5 and the concentrated vapour is introduced into the sterilization chamber 2.

In the second alternative operating mode, which is a continuous concentration process, the pathway between the pre-concentrator 4 and the sterilization chamber 2 is left open. A vapour of a solution of 35% hydrogen peroxide in water enters the pre-concentrator chamber 4 and passes continuously through the pre-concentrator with fan 8 propulsion. As the vapour passes through the pre-concentrator 4, water is preferentially removed. Residence time of the vapour in the pre-concentrator is preferably such that the maximum possible concentration of peroxide is achieved by the time it exits the pre-concentrator.

The vapour may be introduced into the pre-concentrator 4 continuously or intermittently, for example, 2 secs on/18 secs off; or 5 secs on/15 secs off; over a period of, for example, 2 minutes.

However, regardless of whether batch-wise mode a) or continuous mode b) is employed, or even should some combination of continuous or batch wise modes be used, the vapour that exits the pre-concentrator 4 and enter the sterilization chamber 2 is preferably at its maximum achievable hydrogen peroxide concentration.

Once the concentrated vapour is introduced to the sterilization chamber 2, it contacts the article to be sterilized 1 and acts upon the pathogens at the surface. The sterilizing chamber 2 may then be sealed from the pre-concentrator 4. The concentrated vapour is then allowed to contact the article to be sterilized. The article to be sterilized can be stored in the sterilization chamber until needed. This also permits removal of residual hydrogen peroxide and water.

Figure 4:
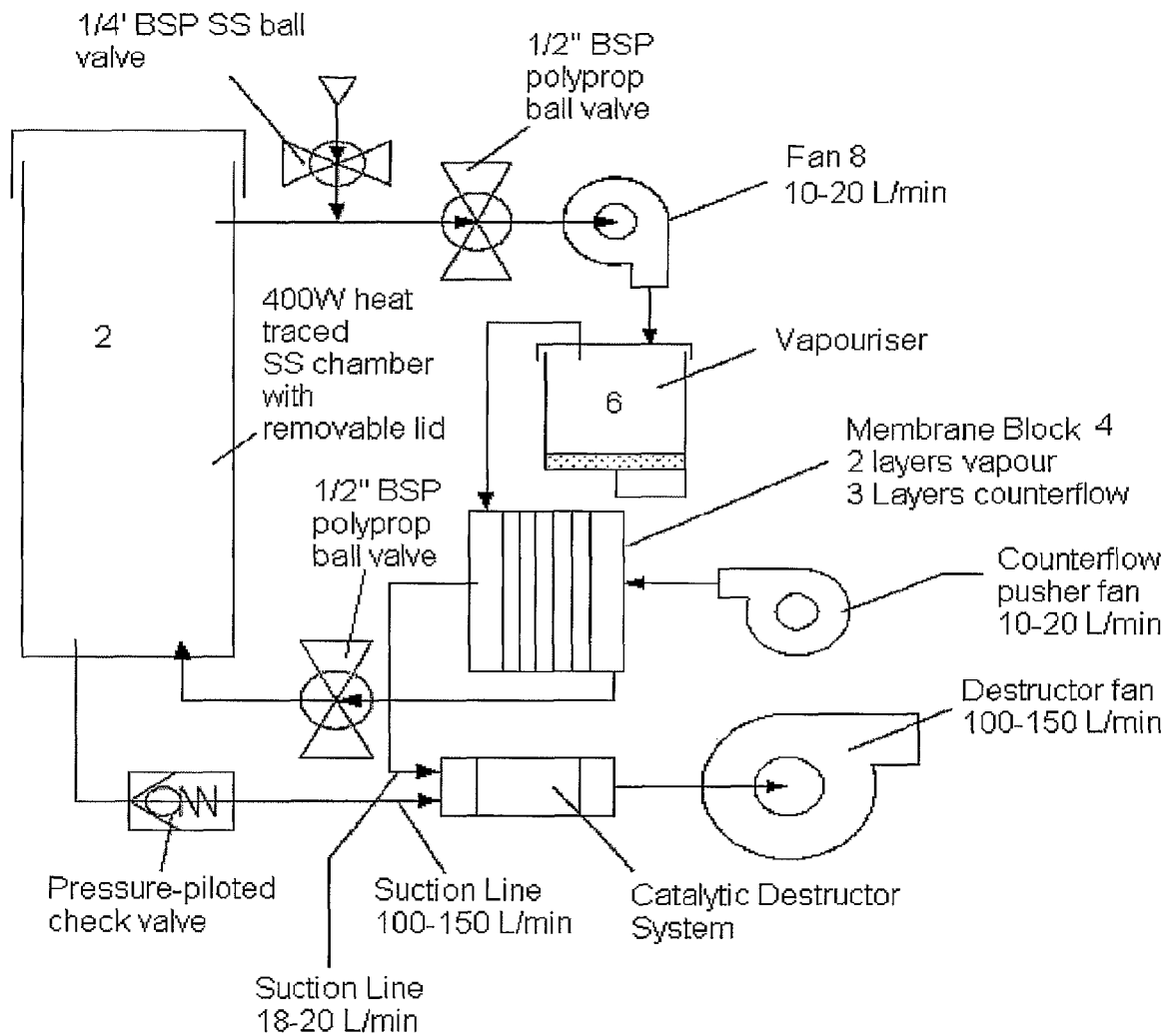
FIG. 4 is a more detailed schematic diagram of a sterilizing apparatus showing the pre-concentrator of the present invention

To expand on each of the steps, and shown in FIG. 4, the cycle commences with vaporization of 27-35% hydrogen peroxide inside a vaporization chamber 6. The vaporizer may function continuously or according to an appropriate duty cycle such that vaporization is intermittent. The vapour has the same composition as the bulk solution from which it was derived.

Once produced, the vapour is transported, by a blower fan 8 into the membrane concentrator system 4 where it is concentrated by means of evaporation.

The membrane concentrator 4 is preferably a multi-layered device where vapour flows over membrane layers which have an alternate airflow on the other side. Selective removal of a proportion of the water vapour occurs in the membrane concentrator due to the differential partial pressures of water and hydrogen peroxide. The vapour exits the concentrator either at a predetermined concentration or "terminally" concentrated such that no further concentration of hydrogen peroxide will occur.

Figure 2:
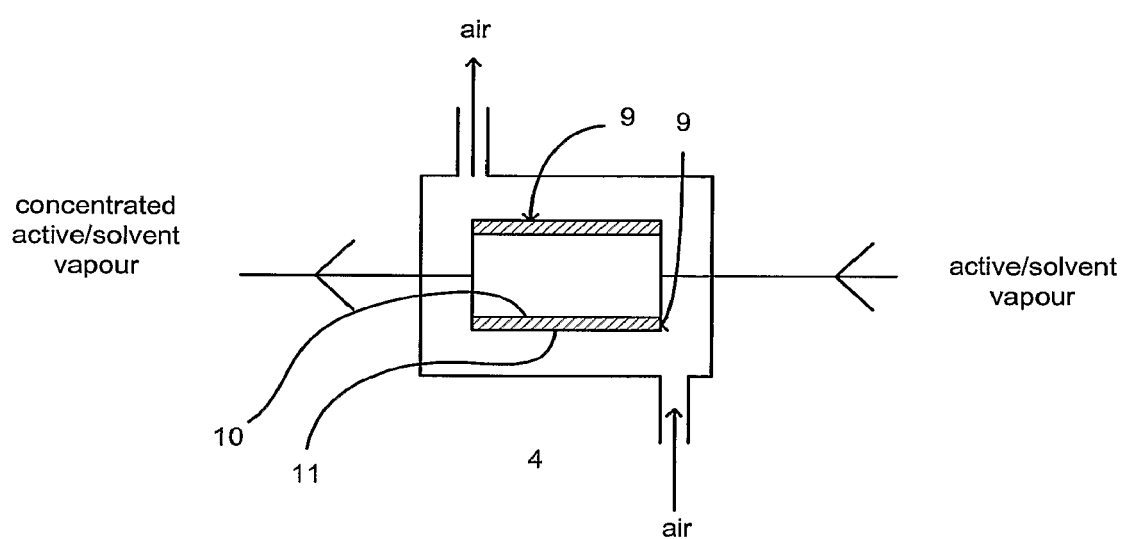
FIG. 2 is diagram of a first simple embodiment of the present invention.
Figure 5:
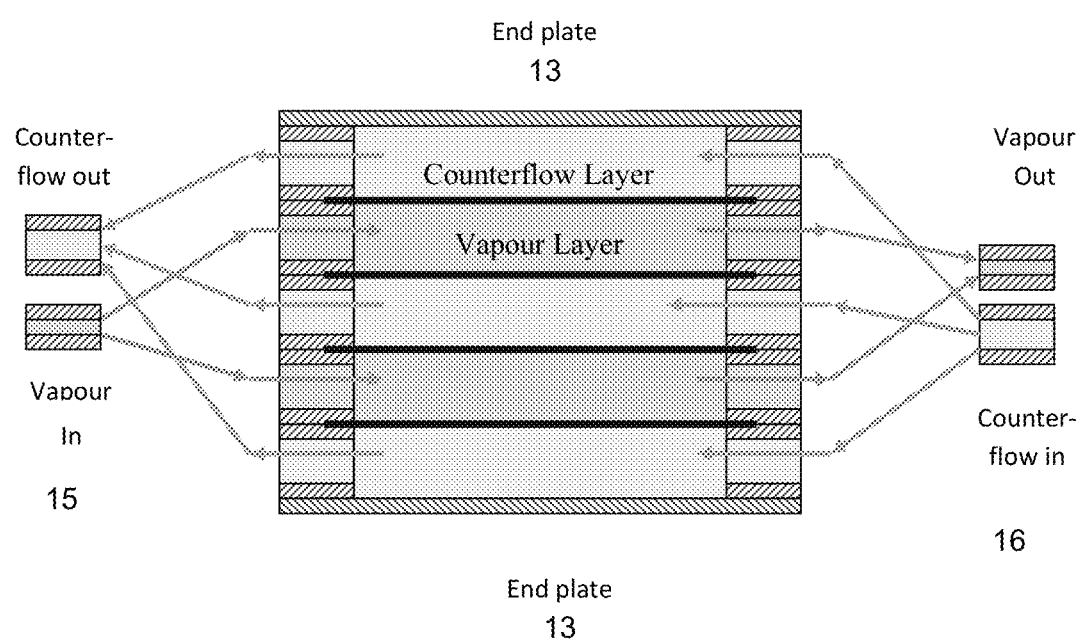
FIG. 5 shows a further embodiment of the present invention.
Figure 6:
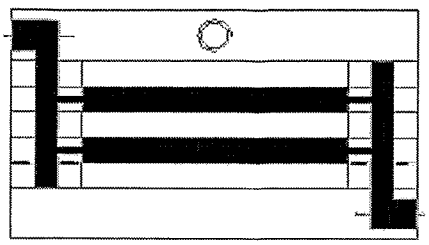
FIG. 6 shows flow patterns of vapour and counter flow in an embodiment of the present invention
Figure 6:
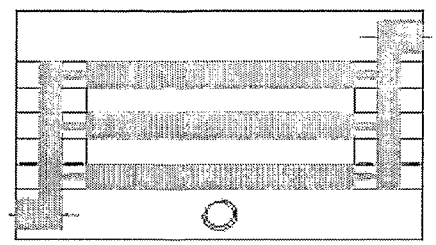
Figure 7:
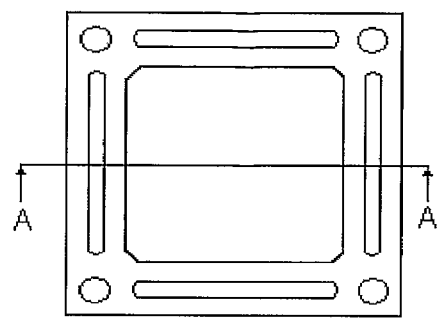
FIG. 7 shows the plates that may be used to separate membranes in those embodiments of the present invention that use stacked arrays.
Figure 7:
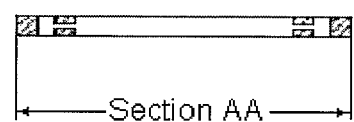
Figure 7:
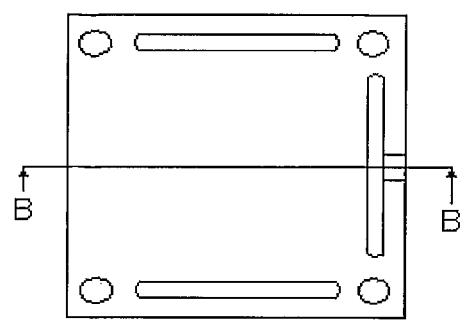
Figure 7:
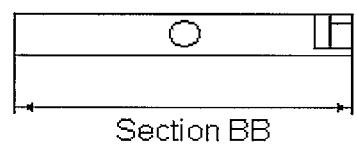
Figure 8:
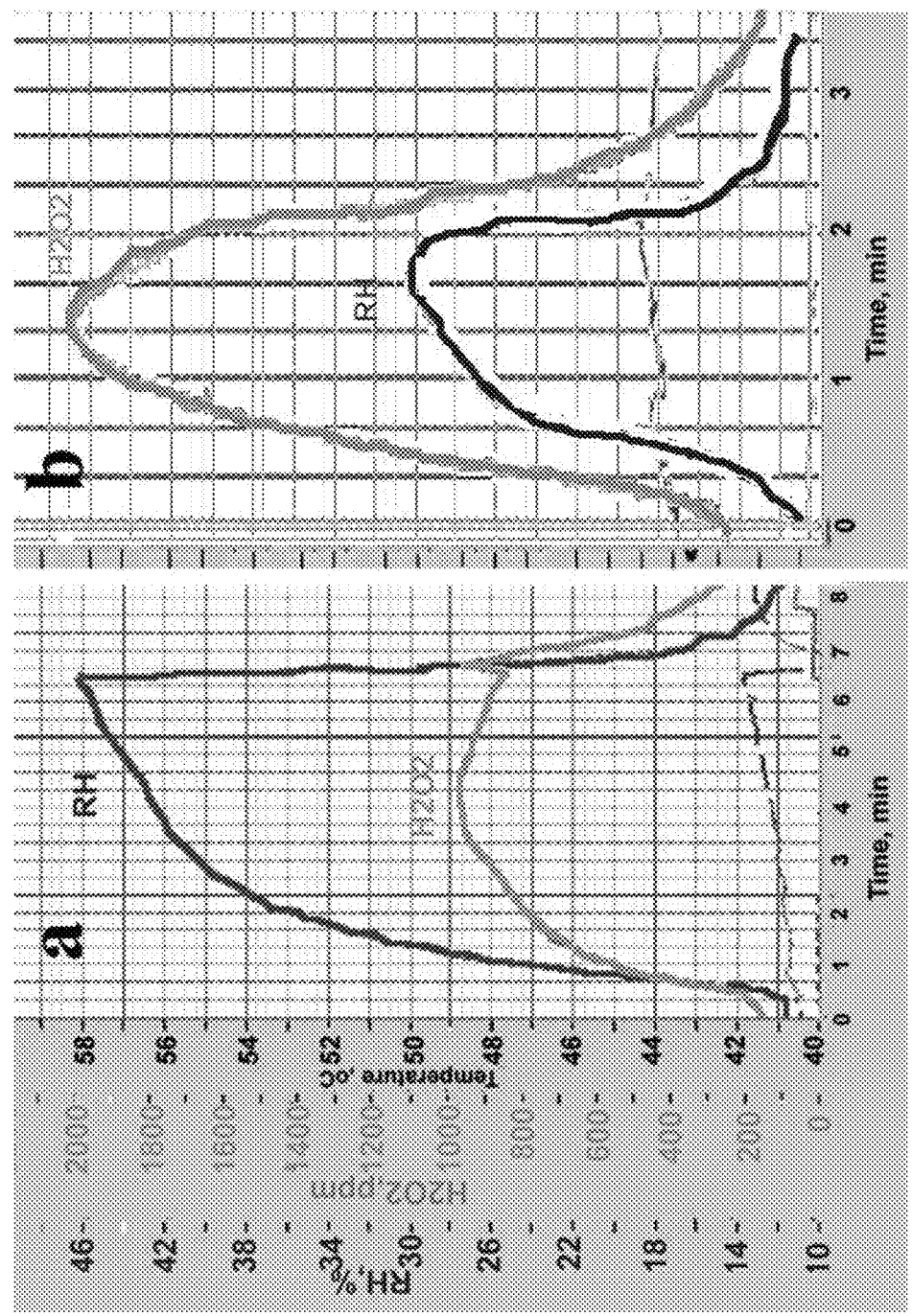
FIG. 8 shows results from a membrane concentrator of the present invention.

In one simple embodiment, seen in FIG. 2, the membrane concentrator is a modular, stackable assembly consisting of 4 main components—flow layer, end plate, tie-rod and membrane sheet. FIG. 5 shows a preferred stack of concentrator modules.

The flow layers 10 and 11 are defined by thin, square or rectangular plates 12 with a large open area inside and four slots (galleries) running parallel to the outer edges, two of which are connected to the inner space via slots. The orientation of the flow layers (when using square sections), determines the number of layers which are common to any particular gallery, hence two distinct flow lines may operate an one single assembly through the method of assembly.

The end plates 13 allow connection of external tubing or devices to the membrane assembly and each end plate has two connection points which correspond to two gallery slots. The slots on these end plates form a manifold which directs flow up one particular gallery per connection and the connections are offset 90 degrees from one another to ensure they access different galleries.

When five flow layers, for example are stacked atop one another with alternate orientations i.e. 90 degrees to each other, and separated by sheets of membrane material, they form two groups of flow layers, one having two flow layers 15 and the other having three separate flow layers 16 within the block. These flow layers are assigned to either vapour (15 in the present case) or crossflow/counterflow (16 in the present case) connections and through regulation of their flow rates, controlled diffusion is possible.

The tie-rods are used to compress the layers between the end plates and create a vapour seal, although any design which allows the blocks to fit together in suitable sealed arrangement may be used. The membrane material 9 also acts as a gasket between the layers.

The vapour pressure of hydrogen peroxide at ambient temperatures is negligible, and water preferentially evaporates in the membrane concentrator. However, as a precaution against any hydrogen peroxide flow exiting the system, the counter flow is taken directly into the catalytic destructor module where it is safely treated.

The membrane 9 in the present example is preferably made of KIMGUARD™, a three layer non linting laminate fabric using polypropylene and having an inner layer which is hydrophobic and resistant to bacterial penetration. The two outer layers provide abrasion resistance and strength. As a multi layered fabric it has no actual pore size, but the fabric is permeable by virtue of microscopic channels which provide a tortuous path limiting passage of particles to those of less than 0.2 micron, ie it is impermeable to micro-organisms below 0.2 microns. This fabric allows hydrogen peroxide vapour or water vapour to permeate through the channels of the fabric. The channels do not permit passage of bacteria into the chamber. Kimguard has a hydrostatic repellency of 3.8 kPa (measure of hydrophobicity) and a cross dimensional tensile load of 70 Newtons and a machine directional tensile load of 130 Newtons.

The membrane 9 may be any other suitable membrane which facilitates the removal of water while being impermeable by micro-organisms. Other fabrics and membranes which are permeable by water vapour and hydrogen peroxide vapours and impenetrable by bacteria may be used, for example TYVEK™ and SPUNGUARD™ (However, KIMGUARD™ has been found to be 2-3 times more permeable to hydrogen peroxide vapour than TYVEK™ under the conditions in which it is used here. As will be discussed hereinafter other membrane materials such as NAFION™ (which is hydrophilic) and the like may also be employed.

NAFION™ is a copolymer of tetrafluoroethylene and perfluoro 3, 6, dioxa-4-methyl-octene-sulphonic acid. Such materials are hydrophilic and have a very high water of hydration. NAFION™ is able to absorb 22% by weight of water. In this variation the absorption proceeds as a first order kinetic reaction. Water molecules pass through the membrane and then evaporate into the surrounding air until equilibrium with the external humidity is reached in a continuous process called pervaporation. An exterior current flow of air over the external side of the membrane provides rapid removal of the moisture from the outside surface and speeds the pervaporation process. Unlike simple permeation wherein the molecules merely diffuse through the open pores, in pervaporation the membrane is active in selectively drawing molecules from one side of the membrane to the other, and may do so at differential rates for differing types of chemical molecule.

Figure 1:
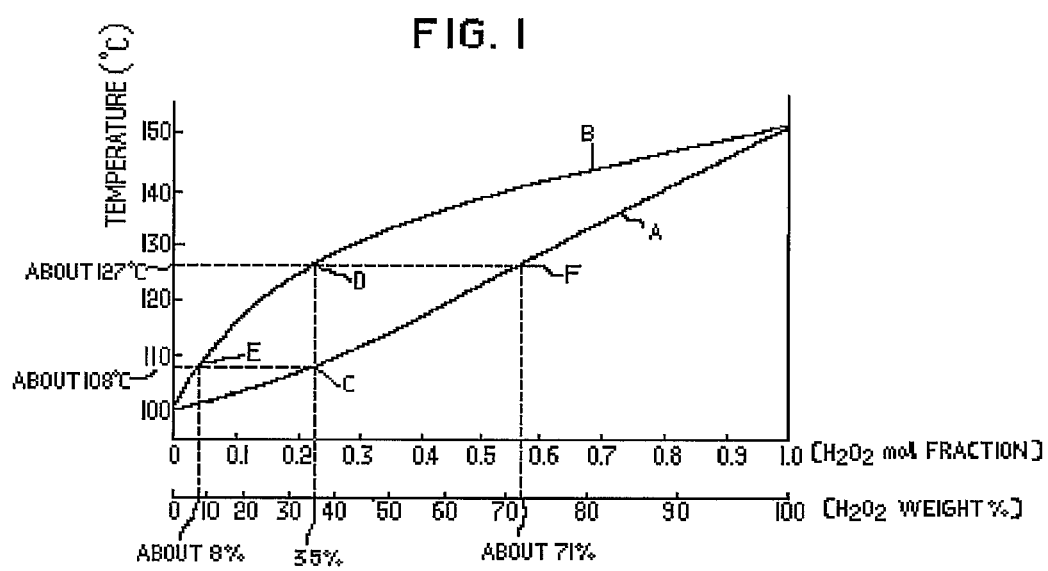
FIG. 1 is a reproduction of a figure from U.S. Pat. No. 4,797,255 which shows (curve A) how the boiling point of a water/peroxide mixture changes with concentration at atmospheric pressure and (curve B) how the gas composition changes.

In the embodiments described above the sterilizing agent is a solution of hydrogen peroxide as a 35 wt % solution in water which acted as the solvent. Water is the preferred solvent for use with peroxide. Water boils at 100° C. while hydrogen peroxide boils at above 151° C. at atmospheric pressure. Hydrogen peroxide boils at 151.4° C. at 760 mm. FIG. 1 taken from U.S. Pat. No. 4,797,255 shows (curve A) how the boiling point at atmospheric pressure of a water/peroxide mixture changes with concentration and (curve B) how the gas composition changes. As is shown, pure water boils at 100° C. at atmospheric pressure. It is evident from FIG. 1 that the concentration of hydrogen peroxide in the vapour at below 100° C. is negligible at atmospheric pressure.

Besides water, the solvent could for example be an aqueous or non-aqueous alcohol chosen in combination with the sterilizing agent to be used. The addition to water of ethyl alcohol results in an azeotropic mixture which lowers the boiling point of the solvent and this enables the water to be "flashed" off at lower temperatures than would otherwise be possible. The addition of other azeotropic agents would be equally beneficial. The use of azeotropes to facilitate the removal of a solvent such as water from the vapour is within the scope of the invention. It is envisaged that for some biocides non-aqueous solvents or a combination of suitable solvents could be employed.

In the case of hydrogen peroxide, as the water flashes off, the concentration of the sterilizing agent increases. If a 35% peroxide solution is used in the invention as the starting material, the resultant vapour will have a concentration of for example 60 to 80% peroxide. This has the advantage that the starting material can be handled relatively safely, that concentration occurs during the process and that thereafter there is no further need to handle the peroxide.

Solutions of a lower or greater concentration than 35% can be used as a starting material and excellent results have been obtained with hydrogen peroxide solutions of 1% or 3% as well as with solutions of 40%. While preferred embodiments described have employed aqueous solutions of hydrogen peroxide as the sterilizing agent, solutions of other peroxides and peroxy compounds can be employed as well as solutions of peroxy complexes (including non water soluble complexes in organic solvents). Sterilizing agents other than peroxides may also be used in the invention, including without limitation halo compounds, phenolic compounds, halogen phenolic compounds and other known biocides, with appropriate choice of solvent.

Figure 9:
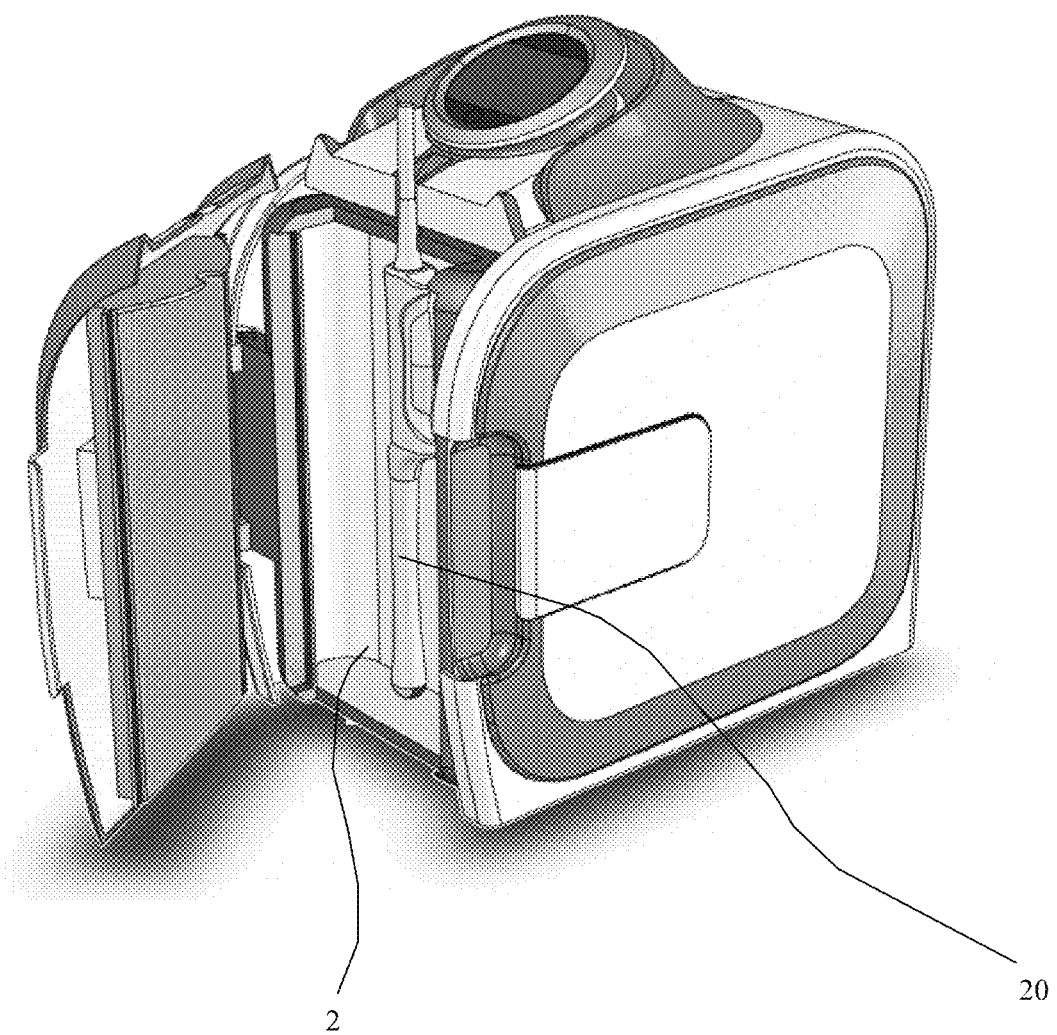
FIG. 9 shows an ultrasonic probe in disinfecting arrangement with a apparatus of the present invention.

In an example in which the article to be disinfected is the part of an ultrasonic probe 20, for example a probe of a type insertable into a body cavity for diagnostic purposes, the part of the probe 20 to be treated is enclosed in a chamber 2 (as exemplified in FIG. 9). In this case the chamber is a specially shaped chamber designed so that the whole article need not be in the chamber, only that part of the probe which is to be treated being enclosed. The probe can be suspended inside the chamber by means of a seal around the gland where the power cord enters the probe.

The vapour is then transported into chamber 2 where it is applied to a target surface. The ultrasound device may be inserted into the chamber via any of the panels on the device. One possible entrance is from the top via a screw top lid into which the cord of the device is clamped and held in place on insertion into the chamber. Passage of the vapour from the concentrator to the chamber is regulated by a check valve 5. Check valves 5 and 12 can control whether the device operates batchwise, continuously or by some combination of both.

If the device operates batchwise, the valve 5 is opened at the appropriate time after the concentration has occurred.

If the device is operated continuously, the valve remains open, with the flow rates and residence times of the vapour calibrated beforehand to be at a maximum when exiting the chamber.

Typically, the chamber 2 is constructed of a heat conductive metal such as stainless steel or aluminium. Various coating may be applied to the interior of the chamber such as Teflon to reduce the risk of peroxide breakdown. The disinfection chamber is electrically heated using heater trace wire applied to the conductive metal surface. Alternatively, or in addition, heated air can be blown into chamber. Chamber atmosphere to supply the blower is made-up from another chamber connection which is placed on the opposite side of the chamber to the inlet. The chamber itself is isolated from the generation and recirculation circuit by means of valves which engage once the vaporization cycle is complete (about 1-1.5 min). This isolation from the adjoining circuit is called "suspended time" or more commonly "hold" time.

The surface of the object 1 to be treated is exposed to the vapour for a time sufficient to sterilize the surface. The resulting concentrated vapour is highly effective at penetrating mated surfaces, and treating occluded surfaces which are not directly exposed.

The chamber 2 may be formed fully of a membrane or fabric or may have a wall of which at least a part is a membrane or fabric may be of any suitable shape and design having regard to the requirements of the process herein described and can be sealed in any manner impenetrable by micro organisms. Other membranes or fabrics can be selected based on the teaching herein provided. The container may be permanently connected to the vaporizer circuit or may be able to be connected and disconnected by a tube and spigot connection, by suitable connectors or other means.

Once the suspended time is complete (approx 1-2 mins), the system moves into catalytic destruction mode or simply "empty". It is in this cycle that a suction fan engages which pilots (opens under pressure) a check valve that connects to the chamber while another valve allows fresh air to enter the chamber at a controlled rate. This cycle moves the vapour into the catalytic destructor module where a catalyst is used to convert the hydrogen peroxide into harmless water vapour and oxygen. The catalytic destructor module is composed of metal oxide baked ceramic honeycomb layers sandwiching similarly treated ceramic beads packaged in a suitable container. The amount of catalyst is proportional to the amount of peroxide extracted from the chamber as well as the flow rate from the chamber. Completion of this cycle takes approximately 1 minute and upon completion, the chamber may be accessed to retrieve the disinfected target device. It is understood that the time to achieve sterilization is more onerous and may take significantly longer.

In some preferred embodiments, the vapour density in the vapour passing from the preconcentrator to the sterilization chamber may be measured by passing an infra red beam across the connecting conduit to a detector and measuring the beam attenuation. The infra red is preferably of a frequency which registers peroxide vapour if any. A knowledge vapour composition, temperature and residence time allows certification of the result if desired.

The preconcentrator can be operated in such a manner that it always outputs vapour comprising peroxide at a predetermined theoretical maximum concentration, thereby avoiding the need to determine the concentration of peroxide at any point of the sterilizing process.

Although the invention has been herein described with reference to hydrogen peroxide as the sterilizing or disinfection agent, the invention could use other peroxides, peroxy-compounds, or complexes of either. Other classes of biocide could be used including without limitation halogenated biocides, phenolic biocides and quaternary compound biocides and it may be advantageous to use solvents other than water. Likewise, although the invention has been herein exemplified primarily with reference to starting solutions having 35% peroxide, other starting concentrations can be employed, although concentrations between about 20% and 35% are preferred.

The principles herein taught could be applied to concentrate the peroxide in such vapour processes by permeation or pervaporation through a membrane, without the need for pressure reduction.

The claims defining the invention are as follows:

1. A method for disinfecting or sterilizing an article comprising:
    vaporizing a solution comprising a biocide comprising hydrogen peroxide or a peroxy compound in a solvent having a first biocide:solvent ratio;
    directing a flow of the vapour at atmospheric pressure or above to a first side of a membrane;
    directing an alternate flow of a gas to a second side of the membrane to increase the first biocide:solvent ratio on the first side of the membrane to a second biocide:solvent ratio greater than the first biocide:solvent ratio thereby producing a concentrated vapour on the first side of the membrane; and
    contacting the article with the concentrated vapour for a time sufficient to disinfect or sterilize it, wherein the solvent has a lower boiling point than the hydrogen peroxide or peroxy compound.

2. The method according to claim 1 wherein the second biocide:solvent ratio is above 60 wt. %.

3. The method according to claim 1 wherein the alternate flow of gas is provided at a rate and for a time such that the second ratio reaches an equilibrium ratio beyond which it will not increase.

4. The method according to claim 1 wherein the membrane is impenetrable by microorganisms.

5. The method according to claim 1 wherein the solvent is water.

6. The method according 1 wherein the biocide comprises hydrogen peroxide.

7. The method according to claim 1 wherein the first biocide:solvent ratio is below 35 wt. %.

8. The method according to claim 1 wherein the second biocide:solvent ratio is above 70 wt. %.

9. The method according to claim 1 wherein the gas is air or humidity conditioned air.

10. The method according to claim 1 wherein the vapour is an aqueous peroxide vapour having an initial concentration of from 6-35 wt. % of peroxide.

11. A method for disinfecting or sterilizing an article comprising:
    enclosing the article inside a container having a wall of which at least a part is a membrane;
    contacting the article with a vapour at atmospheric pressure or above comprising a biocide comprising hydrogen peroxide or a peroxy compound and a solvent and having a first biocide:solvent ratio;
    directing a flow of a gas to a side of the membrane that is external to the container to increase the first biocide:solvent ratio on the first side of the membrane to a second biocide:solvent ratio greater than the first biocide:solvent ratio thereby producing a concentrated vapour; and
    allowing the article to remain in contact with the concentrated vapour for a time sufficient to permit sterilization, wherein the solvent has a lower boiling point than the hydrogen peroxide or peroxy compound.

12. The method according to claim 11 wherein the membrane is impenetrable by microorganisms.

13. The method according 11 wherein the biocide comprises hydrogen peroxide.

14. The method according to claim 11 wherein the first biocide:solvent ratio is below 35 wt. %.

15. The method according to claim 11 wherein the second biocide:solvent ratio is above 70 wt. %.

16. The method according to claim 11 wherein the gas is air or humidity conditioned air.

17. The method according to claim 11 wherein the vapour is an aqueous peroxide vapour having an initial concentration of from 6-35 wt. % of peroxide.

18. The method according to claim 11 wherein the second biocide:solvent ratio is above 60 wt. %.

19. The method according to claim 11 wherein the method further comprises vaporizing a solution comprising the biocide in the solvent.

* * * * *